US012797456B2

(12) United States Patent
Ella et al.

(10) Patent No.: US 12,797,456 B2
(45) Date of Patent: Nov. 17, 2026

(54) MULTIVALENT GLYCOCONJUGATES IMMUNOGENIC COMPOSITIONS

(71) Applicant: BHARAT BIOTECH INTERNATIONAL LIMITED, Hyderabad (IN)

(72) Inventors: Krishna Murthy Ella, Hyderabad (IN); Venkatesan Ramasamy, Hyderabad (IN); Mandalapu Gangadhara Naidu, Hyderabad (IN)

(73) Assignee: BHARAT BIOTECH INTERNATIONAL LIMITED, Hyderabad (IN)

( * ) Notice: Subject to any disclaimer, the term of this patent is extended or adjusted under 35 U.S.C. 154(b) by 304 days.

(21) Appl. No.: 17/292,024

(22) PCT Filed: Nov. 7, 2019

(86) PCT No.: PCT/IN2019/050825
§ 371 (c)(1),
(2) Date: May 7, 2021

(87) PCT Pub. No.: WO2020/095324
PCT Pub. Date: May 14, 2020

(65) Prior Publication Data

US 2021/0401960 A1 Dec. 30, 2021

(30) Foreign Application Priority Data

Nov. 10, 2018 (IN) ............................ 201841017672

(51) Int. Cl.
*A61K 39/112* (2006.01)
*A61K 39/00* (2006.01)
*A61K 39/095* (2006.01)
*A61K 47/64* (2017.01)

(52) U.S. Cl.
CPC ........ *A61K 39/0275* (2013.01); *A61K 39/095* (2013.01); *A61K 47/6415* (2017.08); *A61K 47/646* (2017.08); *A61K 2039/6037* (2013.01); *A61K 2039/6068* (2013.01); *A61K 2039/70* (2013.01)

(58) Field of Classification Search
None
See application file for complete search history.

(56) References Cited

U.S. PATENT DOCUMENTS

| | | | | |
|---|---|---|---|---|
| 3,856,935 | A | 12/1974 | Germanier | |
| 5,738,855 | A | 4/1998 | Szu et al. | |
| 9,011,871 | B2 | 4/2015 | Levine et al. | |
| 9,050,283 | B2 | 6/2015 | Levine et al. | |
| 2004/0258700 | A1* | 12/2004 | Frimann | A61K 47/10 424/278.1 |
| 2013/0129776 | A1 | 5/2013 | Levine et al. | |
| 2016/0263213 | A1* | 9/2016 | Maclennan | A61K 47/6415 |

FOREIGN PATENT DOCUMENTS

| | | | | |
|---|---|---|---|---|
| CN | 1404873 | A | 3/2003 | |
| EP | 2870974 | A1 * | 5/2015 | A61K 39/0275 |
| WO | WO-2010083477 | A2 * | 7/2010 | A61K 39/0275 |
| WO | WO-2012049662 | A1 * | 4/2012 | A61K 39/0275 |
| WO | 2015029056 | A1 | 3/2015 | |
| WO | WO-2016168324 | A1 * | 10/2016 | A61K 39/02 |

OTHER PUBLICATIONS

Smith, Emma. Halting the Spread of *Salmonella*, Oct. 12, 2018. https://www.ovg.ox.ac.uk/news/halting-the-spread-of-salmonella retrieved on Sep. 17, 2023.*
Fiorino et al. Front. Immunol. 8:168, pp. 1-11, Feb. 27, 2017.*
Module 2: Vaccines and drugs: similarities and differences. 30 pages. Retrieved from https://isoponline.org/wp-content/uploads/2015/10/Differences-on-drugs-and-vaccines.pdf on Sep. 17, 2023.*
Simon et al. Infection and Immunity, vol. 79, No. 10, p. 4240-4249.*
An et al. Vaccine 29 (2011) 7618-7623.*
Baliban et al.: Immunogenicity and Induction of Functional Antibodies in Rabbits Immunized with a Trivalent Typhoid-Invasive Nontyphoidal *Salmonella* Glycoconjugate Formulation, Molecules, Jul. 17, 2018, 23, 1749. Whole document esp. Abstract & Materials and Methods.
Fiorino et al.: Immunogenicity of a bivalent adjuvanted glycoconjugate vaccine against *Salmonella typhimurium* and *Salmonella enteritidis*, Frontiers in Immunology, Feb. 27, 2017, vol. 8, article 168. Whole document esp. Abstract & Materials and Methods.
International Search Report and Written Opinion issued Feb. 14, 2020 for PCT/IN2019/050825.
Crump et al., "A Perspective on Invasive *Salmonella* Disease in Africa" Clin. Infect. Dis. 61(Suppl. 4), S235-S240.

* cited by examiner

*Primary Examiner* — Oluwatosin A Ogunbiyi
(74) *Attorney, Agent, or Firm* — Schmeiser Olsen PLLC

(57) ABSTRACT

Provided are multivalent conjugate compositions against *Salmonella* diseases. A combined vaccine composition of glycol-conjugates in tetravalent, trivalent and bivalent combinations are disclosed.

17 Claims, 3 Drawing Sheets

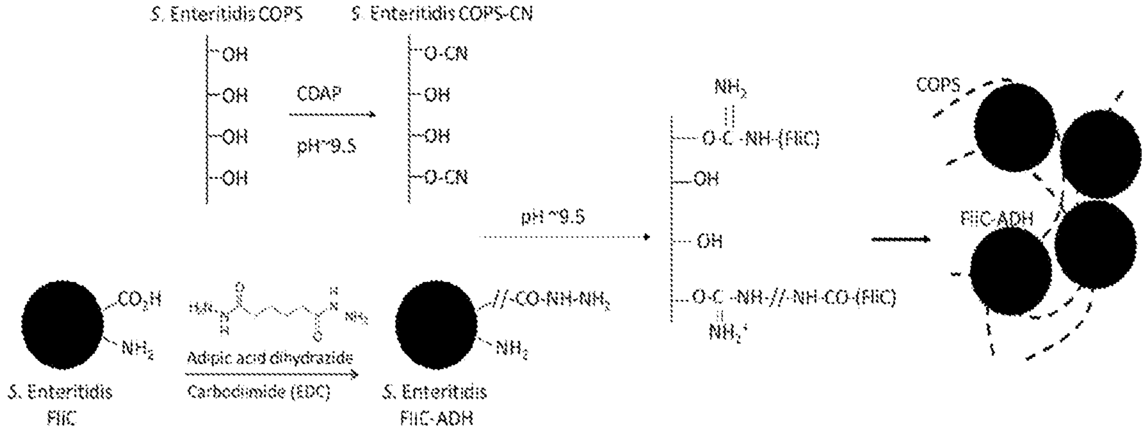
**Figure 1: Overview of the process for chemical synthesis of the *S.* Enteritidis COPS: FliC conjugate**

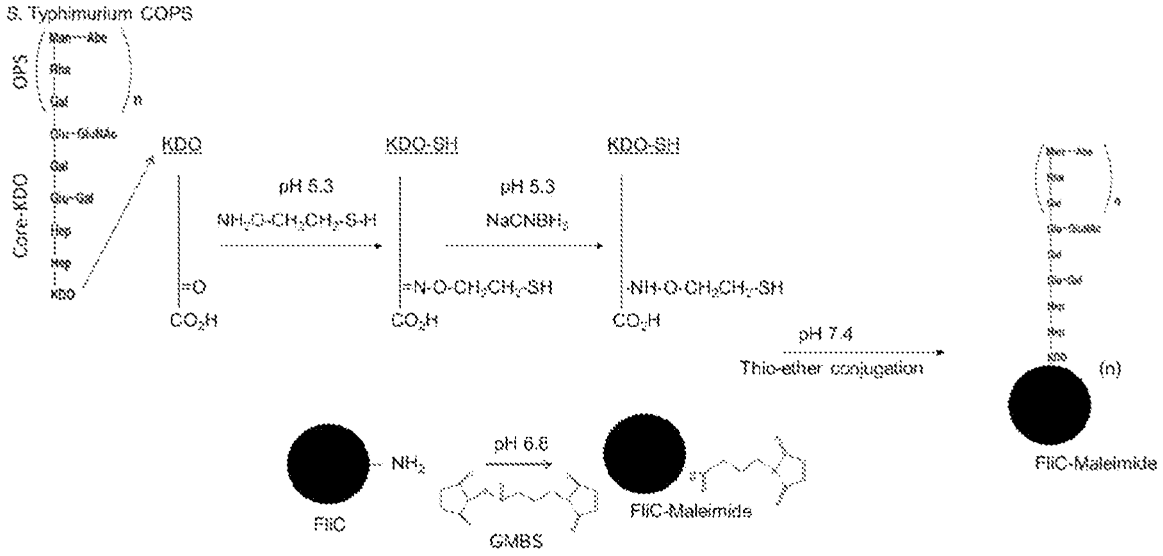
**Figure 2: Overview of the process for chemical synthesis of the *S.* Typhimurium COPS:FliC conjugate**

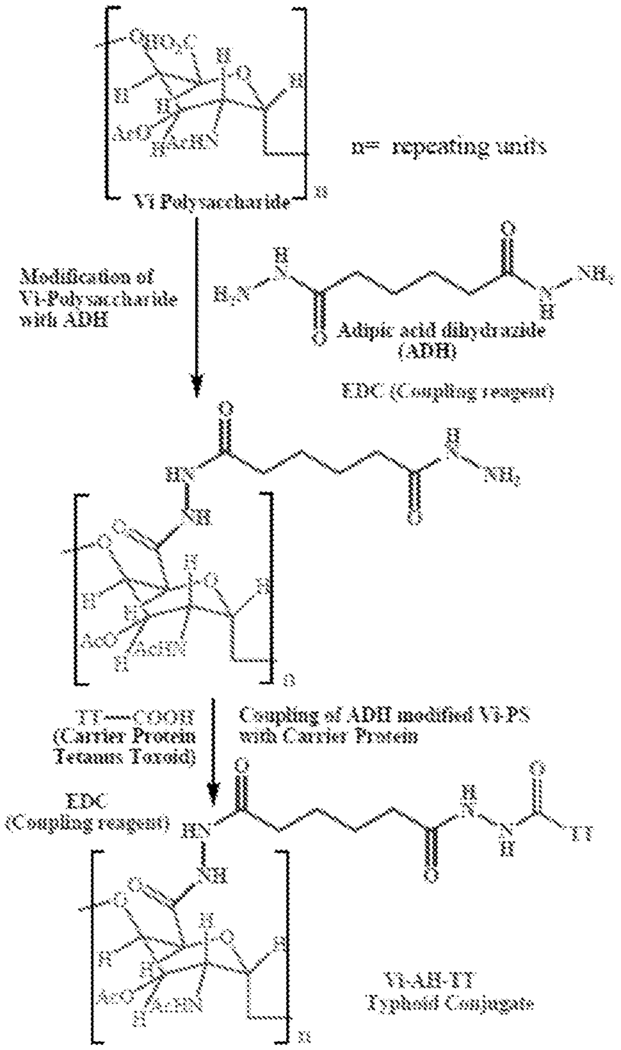
**Figure 3: Overview of the process for chemical synthesis of *S.* TyphiVi-TT (Typbar-TCV™) conjugate**

MULTIVALENT GLYCOCONJUGATES IMMUNOGENIC COMPOSITIONS

CROSS-REFERENCE TO RELATED APPLICATIONS

This application claims priority to PCT Application No. PCT/IN2019/050825, having a filing date of Nov. 7, 2019, which is based on IN 201841017672, having a filing date of Nov. 10, 2018, the entire contents both of which are hereby incorporated by reference.

FIELD OF TECHNOLOGY

The following is related to the field of polysaccharide conjugate immunogenic compositions such as vaccines. More particularly, to the field of polysaccharide conjugate compositions. The combined conjugate vaccine compositions of this present invention is for prophylaxis against infections caused by *Salmonella* and Non-typhoidal *Salmonella* infections that cause typhoid fever.

BACKGROUND

In humans, the infection caused by *Salmonella enterica* depends primarily on the infecting serovar. The majority of invasive infections causing typhoid fever is from the serovar known as *Salmonella enterica* serotype *Typhi* (*S. typhi*); *S. enterica* serotypes Paratyphi A, B, and C.

*Salmonella enterica* is a motile aerobic or facultatively anaerobic, gram-negative *bacillus*, nonspore-forming bacteria known to cause clinical infections. *Salmonella enterica* encompasses more than 2500 sero-variants which are known to cause human clinical infections. Serovar *S. typhi*, a human-restricted pathogen, causes typhoid fever, which is characterized by fever, abdominal discomfort and frontal headaches. These sero-variants include both typhoidal serovars and non-typhoidal serovars. For instance, serovars such as *Salmonella enterica* serovar *Typhimurium* (S. *Typhimurium*) cause self-limiting gastroenteritis, while *Salmonella enterica* serovar *Typhi* (*S. typhi*) result in typhoid fever.

These typhoidal serovariants were known to cause clinical infection in human but the non-typhoidal serovars (NTS) can cause invasive clinical disease in infants, immunosenescent elderly and immune-compromised people. Hence together these serovariants are responsible for notable drift on the morbidity and mortality rate across the world.

The Sub-Saharan populations especially children seem to be more affected with both the typhoid and invasive NTS (iNTS) disease, wherein school age children are more affected with typhoid while infants and toddlers were attacked and affected by iNTS. Nontyphoidal *Salmonella* can be invasive and cause paratyphoid fever, which requires immediate treatment with antibiotics. In Saharan Africa, iNTS infections are mainly caused by serovars such as *S. enteritidis* and *S. typhimurium* which results in fatality rates of 12-28%.

Some regions exhibit only typhoid disease whereas others only iNTS, and yet others have both types of infections, indicating variability in geographic prevalence. The iNTS strains which are found in sub-Saharan Africa are fundamentally distinct from the conventional gastroenteritis NTS strains which are found in the USA and Europe.

Analyses of *S. typhimurium* and *S. enteritidis* revealed novel multi-locus sequence types and patterns of genetic degradation analogous to those present in typhoid and paratyphoid serovars. Pathotypic analyses of a prototype sub-Saharan African *S. typhimurium* blood isolate found reduced inflammation and enhanced intracellular survival in cultured cells, and the absence of diarrhea in a non-human primate model—phenotypes generally associated with *S. typhi.*

Despite ongoing research efforts, the reservoir for iNTS infection has not yet been identified, hampering the ability to implement traditional environmental interventions for interruption of transmission, Crump et al., "*A Perspective on Invasive Salmonella Disease in Africa*" Clin. Infect. Dis. 61(Suppl. 4), S235-S240 (available on-line Oct. 7, 2015). Although several types of typhoid vaccines are available, no human NTS vaccines are currently in use.

U.S. Pat. No. 5,738,855 (Shousun Chen Szu et al.) teaches the method of making a modified saccharide and immunogenic conjugate. It can be a modified plant, fruit or synthetic oligosaccharide or polysaccharide which has been structurally altered so as to render the modified saccharide antigenically similar to the Vi of *Salmonella typhi*. The modified saccharide may be conjugated to a carrier to form a conjugate that is immunogenic against *S. typhi*. Antibodies produced in response to the immunogenic conjugate are protective against typhoid fever.

U.S. Pat. No. 3,856,935 (R Germanier) teaches about the oral typhoid vaccine and the method of preparing a vaccine thereof using *Salmonella typhi* strain ty 2 which is subjected to ultraviolet light. The mutants so produced are screened for selection of strains defective in the enzyme uridine diphosphogalactose-4-epimerase. A live vaccine is prepared from the selected and carefully isolated strains in the usual manner. The strains are also identified by their sharply reduced galactokinase and galactose-1-phosphate uridylyl transferase activity, as compared to the parent strain.

China Patent No. 1404873A teaches that the typhoid Vi polysaccharide is covalently conjugated on the carrier protein to form conjugative vaccine that can be used to generate active immunity in humans and other mammals, and for preventing typhoid infection. After the typhoid Vi polysaccharide is conjugated with protein, the recognition mode of organism to typhoid Vi antigen is changed into T cell depended antigen that can be used for immunity of all people and possesses obvious effect for boosting immunity.

U.S. Pat. No. 9,011,871 (Myron M. et al.) teaches about a multivalent *Salmonella enterica* serovar conjugate vaccines comprising conjugates of *S. typhimurium, S. enteritidis, S. choleraesuis, S. typhi, S. paratyphi* A and *S. paratyphi* B, wherein the conjugates comprise a hapten antigen and a carrier antigen, wherein at least one of the hapten antigens or carrier antigens is characteristic of the *Salmonella enterica* serovar. The disclosure also provides *Salmonella enterica* serovar reagent strains to produce the multivalent conjugate vaccines and attenuated *Salmonella enterica* serovars for use as vaccines.

U.S. Pat. No. 9,050,283 (Myron M. et al.) is drawn to attenuated *Salmonella* serovar strains *S. typhimurium* and *S. enteritidis*, conjugate vaccines derived from these attenuated strains of *S. typhimurium* and *S. enteritidis*, comprising an O polysaccharide covalently linked to a flagellin protein, and methods for inducing an immune response in a subject.

WO 2015/029056 A1 (Ella et al.) teaches stable conjugate vaccine formulations for protections against *Salmonella typhii*, and methods of conjugation between Vi-polysaccharide of *S. typhii* to tetanus toxoid as the carrier protein, responsible for producing improved T-dependent immune response against Typhoid fever caused by *Salmonella typhi*. The methods disclosed in embodiments of the invention and the resulting formulations are capable of inducing immunity against typhoid fever including in children below 2 years of age, through only a single injection to comprise a complete vaccination schedule.

A conjugate vaccine against typhoid Vi (Typbar-TCV®) was distributed in 2013. That vaccine has been given to large numbers of infants, toddlers, children and adults in India and also other countries. Thus, there is already a substantial track record of safety and immunogenicity for Typbar-TCV®.

Although different forms of typhoid vaccines are in use, no human NTS vaccines are available. Thus, there is a need in the field for immunogenic compositions that provide protection against *Salmonella* infections, which cause typhoid, and Non-typhoidal *Salmonella* infections (NTS), which cause paratyphoid fever.

SUMMARY

An aspect relates to an immunogenic composition comprising two or more of antigen of typhoidal serovars and/or non-typhoidal serovars of *Salmonella*, wherein each antigen is conjugated to one or more carrier molecules.

Another aspect is to provide a method for preventing or treating a *Salmonella* infection comprising administering to a patient an effective amount of the immunogenic composition comprising antigens of two or more typhoidal serovars and/or non-typhoidal serovars of *Salmonella*.

Yet another aspect is to provide a method for manufacturing immunogenic composition comprising antigens of two or more typhoidal serovars and/or non-typhoidal serovars of *Salmonella*.

Embodiments of the invention are directed to polysaccharide conjugate immunogenic compositions, and combined immunogenic compositions of polysaccharide conjugate immunogenic compositions. Compositions of embodiments of the invention provide prophylaxis against infections caused by *Salmonella* and Non-typhoidal *Salmonella* infections that cause typhoid fever. Types of *Salmonella* and Non-typhoidal *Salmonella* infections that can be treated or prevented include but are not limited to infections of *Salmonella enteritidis, Salmonella typhimurium, Salmonella typhi, Salmonella paratyphi* A, B and/or C, and combinations thereof. Immunogenic compositions may also be generated for the prophylaxis or treatment of Meningococcal infections.

The main aspect of embodiments of the invention is to provide an immunogenic composition comprising two or more of:

- an antigen of *Salmonella enteritidis;*
- an antigen of *Salmonella typhimurium;*
- an antigen of *Salmonella typhi*; and/or
- an antigen of *Salmonella paratyphi*, wherein each antigen is conjugated to one or more carrier molecules.

In some embodiment, there is provided the above described immunogenic composition, wherein the one or more carrier molecules comprises one or more of tetanus toxin, tetanus toxin heavy chain proteins, diphtheria toxoid, tetanus toxoid, *Pseudomonas* exoprotein A, *Pseudomonas aeruginosa* toxoid, *Bordetella pertusis* toxoid, *Clostridium perfringens* toxoid, *Escherichia coli* heat-labile toxin B subunit, *Neisseria meningitidis* outer membrane complex, rEPA, *Hemophilus influenzae* protein D, Flagellin Fli C, Horseshoe crab Haemocyanin, and fragments, derivatives, and modifications thereof.

In some embodiment, the immunogenic composition comprises a pharmaceutically acceptable buffer such as PBS and Tween 80.

In some embodiment, the immunogenic composition comprises a stabilizer such as 2-phenoxy ethanol.

In some embodiment, the immunogenic composition comprises an adjuvant.

In some embodiment, each of the antigenic conjugate is present in the immunogenic composition at a dose range of about 5 μg/dose to about 30 μg/dose.

In some embodiment, the immunogenic composition comprises two antigenic components selected form the following:

a. the antigen of *Salmonella enteritidis* and the antigen of *Salmonella typhimurium;*
b. the antigen of *Salmonella enteritidis* and the antigen of *Salmonella typhi;*
c. the antigen of *Salmonella enteritidis* and the antigen of *Salmonella* paratyphi;
d. the antigen of *Salmonella typhimurium* and the antigen of *Salmonella typhi*; or
e. the antigen of *Salmonella typhimurium* and the antigen of *Salmonella* paratyphi.

In some embodiment, the immunogenic composition comprises three antigenic components selected form the following:

a. the antigen of *Salmonella enteritidis*, the antigen of *Salmonella typhimurium* and the antigen of *Salmonella typhi;*
b. three antigenic components, the antigen of *Salmonella enteritidis*, the antigen of *Salmonella typhimurium* and the antigen of *Salmonella paratyphi*; or
c. the antigen of *Salmonella typhimurium*, the antigen of *Salmonella typhi*, and the antigen of *Salmonella paratyphi.*

In another aspect, there is provided a method for preventing or treating a *Salmonella* infection comprising administering to a patient an effective amount of the immunogenic composition according to embodiments of the invention. In some embodiments, there is provided a method for preventing or treating a *Salmonella* infection comprising parenteral administration to a patient an effective amount of the immunogenic composition according to embodiments of the present invention. In some other embodiment. In some embodiment, there is provided a method for preventing or treating a *Salmonella* infection comprising administering to a patient an effective amount of the immunogenic composition according to embodiments of the present invention, wherein administration results in an eight-fold rise in antibody titer.

In yet another aspect, there is provided a method for the manufacture of the immunogenic composition, comprising:

- providing the at least two antigens;
- conjugating each of the at least two antigens to a carrier molecule; and
- preparing each conjugate at a dose of about 5 μg/dose to about 30 μg/dose.

In some embodiment, the conjugation method for the manufacture of the immunogenic composition is performed by:

- carbodiimide mediated modification of the antigen with adipic acid dihydrazide (ADH) introducing reactive hydrazide groups that are then used to link to the carrier molecule via a second carbodiimide step;
- derivatization of the antigen with the amine reactive reagent succinimidyl 4-maleimidylbutyrate (GMBS) that introduces a maleimide moiety that is then linked to a reactive sulfhydryl of the derivatized molecule via formation of a thio ether bond; or
- CDAP chemistry.

One embodiment of the invention is directed to combination conjugate immunogenic compositions comprises one or more of: an antigen of *Salmonella enteritidis*; an antigen of *Salmonella typhimurium*; an antigen of *Salmonella typhi*; an antigen of *Salmonella paratyphi* A; and an antigen of a non-typhoidal *Salmonella* microorganism, with each antigen conjugated to a carrier protein or peptide. The antigen for each may comprise an isolated immunogenic portion of the microorganism such as a polysaccharide, and/or capsular polysaccharide, and/or a portion of or a whole attenuated microorganism, In an embodiment, the carrier proteins or peptides of the immunogenic composition comprises one or more of tetanus toxin, tetanus toxin heavy chain proteins, diphtheria toxoid, tetanus toxoid, *Pseudomonas* exoprotein A, *Pseudomonas aeruginosa* toxoid, *Bordetella pertusis* toxoid, *Clostridium perfringens* toxoid, *Escherichia coli* heat-labile toxin B subunit, *Neisseria meningitidis* outer membrane complex, rEPA, *Hemophilus influenzae* protein D, Flagellin FliC, Horseshoe crab Haemocyanin, and fragments, derivatives, and modifications thereof, or another conventional protein conjugate. In an embodiment each conjugate of the immunogenic composition is formulated at a dose range of from about 5 μg/dose to about 30 μg/dose. Also, In an embodiment, the composition contains a pharmaceutically acceptable stabilizer and/or a pharmaceutically acceptable buffer. Stabilizers include, for example, 2-phenoxy ethanol, and buffers include, but are not limited to PBS buffers with or without a non-ionic detergent, such as, for example Tween 80 and at a pH of about 6.5 to about 7.5.

In an embodiment, the immunogenic composition comprises two or more of: an antigen of *Salmonella enteritidis* conjugated to a first carrier protein; an antigen of *Salmonella typhimurium* conjugated to a second carrier protein or peptide; an antigen of *Salmonella typhi* conjugated to a third carrier protein or peptide; an antigen of *Salmonella paratyphi* A conjugated to a fourth carrier protein or peptide, and an antigen of a non-typhoidal *Salmonella* microorganism conjugated to a fifth carrier protein or peptide, the immunogenic composition comprises three or more of an antigen of *Salmonella enteritidis* conjugated to a first carrier protein; an antigen of *Salmonella typhimurium* conjugated to a second carrier protein or peptide; an antigen of *Salmonella typhi* conjugated to a third carrier protein or peptide, an antigen of *Salmonella* paratyphi A conjugated to a fourth carrier protein or peptide, and an antigen of a non-typhoidal *Salmonella* microorganism conjugated to a fifth carrier protein or peptide. Each carrier molecule may be the same or different. Especially combinations comprise an antigen from each of *Salmonella enteritidis, Salmonella typhimurium*, and *Salmonella typhi*, or an antigen from each of *Salmonella enteritidis* and *Salmonella typhimurium*, or an antigen from each of *Salmonella typhi* Vi and *Salmonella paratyphi* A.

Another embodiment of the invention comprises one or more antigens of a Meningococcal microorganism, such as a polysaccharide or glycoconjugate that may be combined with any other immunogenic compositions of this disclosure.

Other embodiments and advantages of the invention are set forth in part in the description, which follows, and in part, may be obvious from this description, or may be learned from the practice of embodiments of the invention.

BRIEF DESCRIPTION

Some of the embodiments will be described in detail, with references to the following Figures, wherein like designations denote like members, wherein:

FIG. 1 gives an overview of the process for chemical synthesis of the *S. Enteritidis* COPS:FliC conjugate;

FIG. 2 gives an overview of the process for chemical synthesis of the *S. Typhimurium* COPS:FliC conjugate; and FIG. 3 gives an overview of the process for chemical synthesis of S. TyphiVi-TT (Typbar-TCV™) conjugate.

DETAILED DESCRIPTION

Typhoid fever, also known simply as typhoid, is a bacterial infection attributed to *Salmonella*. These bacteria colonize the intestines and blood of affected individuals causing significant morbidity and mortality. In 2000, typhoid fever caused an estimated 21.7 million illnesses and approximately 217,000 deaths, most often in children and young adults between 5 and 19 years old. The species and subspecies of *Salmonella* generally responsible include *Salmonella enteritidis, Salmonella typhimurium, Salmonella typhi, Salmonella* paratyphi, and the multiple serotypes or serovars of each. The two main types of the subspecies *enterica* are ST1 and ST2, based on MLST subtyping scheme. Non-typhoidal serovars (NTS) of *Salmonella* cause invasive clinical disease especially in infants, the elderly and immune-compromised individuals. Although a vaccine against typhoid fever exist, there are currently no vaccines against iNTS and many of the different serovars. The typhoid vaccines which are globally available are generally impractical for administration to the most vulnerable such as infants and the elderly.

Immunogenic composition comprised of typhoidal serovars and/or non-typhoidal serovars of *Salmonella*, and methods for the manufacture and use of these immunogenic compositions, have been surprisingly discovered that are effective for the prevention and/or treatment of *Salmonella* infections and, in particular, for prevention and/or treatment of infections caused by *S. enteritidis, S. typhimurium, S. typhi, S. partyphi* A, B and C, NTS and iNTS. The immunogenic composition comprises one or more of: an antigen of *Salmonella enteritidis*; an antigen of *Salmonella typhimurium*; an antigen of *Salmonella typhi*; an antigen of *Salmonella* paratyphi A; and an antigen of a non-typhoidal *Salmonella* microorganism, with each antigen conjugated to a carrier protein or peptide. The antigen for each may comprise an isolated immunogenic portion of the microorganism such as an immunogenic polysaccharide, and/or capsular polysaccharide, and/or a portion of or a whole attenuated microorganism. In an embodiment, the carrier proteins or peptides of the immunogenic composition comprises one or more of tetanus toxin, tetanus toxin heavy chain proteins, diphtheria toxoid, tetanus toxoid, *Pseudomonas* exoprotein A, *Pseudomonas aeruginosa* toxoid, *Bordetella pertussis* toxoid, *Clostridium perfringens* toxoid, *Escherichia coli* heat-labile toxin B subunit, *Neisseria meningitidis* outer membrane complex, rEPA, *Hemophilus influenzae* protein D, Flagellin Fli C, Horseshoe crab Hemocyanin, and fragments, derivatives, and modifications thereof, or another conventional protein conjugate. In an embodiment, each antigen is conjugated to a carrier protein or peptide, although multiple antigenic components may be conjugated to the same or multiple carrier molecules. Conjugation of polysaccharides to protein carriers typically improves immunogenicity. In an embodiment the conjugation involves coupling via a conventional conjugation procedure, such as, for example, cyanylating agent such as, for example, 1-cyano-4-(dimethylamino)-pyridinium tetrafluoroborate (CDAP), 1-cyanobenzotriazole (1-CBT), 2-cyanopyridazine-3 (2H)-One (2-CPO), 1-cyanoimidazole (1-CI), 1-cyano-4-pyrrolidinopyridinium tetrafluorborate (CPPT), carbodiimide mediated modification of the polysaccharide with adipic acid dihydrazide (ADH) treatment of the carrier, modification at the polysaccharide terminal 2-keto-3-deoxyoctonate (KDO) carbonyl with an aminooxy thiol linker that forms an oxime bond with the KDO ketone that is further reduced with sodium cyanoborohydride, antigen derivatized with the amine reactive reagent succinimidyl 4-maleimidylbutyrate (GMBS) to introduce a maleimide moiety that is then linked to the reactive sulfhydryl of the derivatized COPS molecule via formation of a thio ether bond, or a modification thereof.

In some embodiment, the immunogenic composition comprises two antigenic components selected form the following:

a. the antigen of *Salmonella enteritidis* and the antigen of *Salmonella typhimurium;*
b. the antigen of *Salmonella enteritidis* and the antigen of *Salmonella typhi;*
c. the antigen of *Salmonella enteritidis* and the antigen of *Salmonella* paratyphi;
d. the antigen of *Salmonella typhimurium* and the antigen of *Salmonella typhi*; or
e. the antigen of *Salmonella typhimurium* and the antigen of *Salmonella* paratyphi.

In some embodiment, the immunogenic composition comprises three antigenic components selected form the following:

a. the antigen of *Salmonella enteritidis*, the antigen of *Salmonella typhimurium* and the antigen of *Salmonella typhi;*
b. three antigenic components, the antigen of *Salmonella enteritidis*, the antigen of *Salmonella typhimurium* and the antigen of *Salmonella paratyphi*; or
c. the antigen of *Salmonella typhimurium*, the antigen of *Salmonella typhi*, and the antigen of *Salmonella* paratyphi.

In an embodiment, the composition contains one or more of a pharmaceutically acceptable stabilizer (e.g., 2-phenoxy ethanol), buffer, protecting agent such as a preservative (e.g., Thiomersal), amino acid, salt, bulking agent, antioxidant, and/or dispersant. Stabilizers and protecting agents are used to help the composition maintain effectiveness during manufacture and/or storage and, in particular, where transportation conditions may be an issue. Instability can cause loss of antigenicity and decreased effectiveness. Factors affecting stability include temperature, pH, hydrolysis and protein or polysaccharide aggregation, for example. Stabilizing agents include, for example, pharmaceutically acceptable sugars, gelatins, amino acids, alcohols, oils, and salts. Stabilizers include, for example, 2-phenoxy ethanol, and buffers include, but are not limited to, PBS (phosphate buffered saline) buffers with or without a non-ionic detergent, which is based on a polyoxyethylene or a glycoside. Non-ionic detergents include, for example, Tween (e.g., Tween 20; Tween 80), Triton (e.g., TX-100), and the Brij series of detergents. In an embodiment, the pH of the composition is from about 5.0 to about 8.5, from about 6.0 to about 8.0, or from about 6.5 to about 7.5. In an embodiment each conjugate of the immunogenic composition is formulated at a dose range of from about 1 μg/dose to about 100 μg/dose, from about 2.5 μg/dose to about 50 μg/dose, or from about 5 μg/dose to about 30 μg/dose, although individual patients and situations may warrant more of less per dose.

In an embodiment, immunogenic compositions of embodiments of the invention may include adjuvants. An adjuvant is a pharmacological or immunological agent that modifies the effect of other agents. Adjuvants may be added to a vaccine to boost the immune response to produce more antibodies and longer-lasting immunity, thus minimizing the dose of antigen needed. Adjuvants may also be used to enhance the efficacy of a vaccine by helping to modify the immune response to particular types of immune system cells: for example, by activating T cells instead of antibody-secreting B cells depending on the purpose of the vaccine. Adjuvants include, but are not limited to analgesic adjuvants, inorganic compounds such as alum, aluminium hydroxide, aluminium phosphate, calcium phosphate hydroxide, mineral oil, paraffin oil, bacterial products such as killed bacteria (e.g., *Bordetella pertussis, Mycobacterium bovis*, bacterial toxoids), cytokines (e.g., IL-1, IL-2, IL-12), Freund's complete adjuvant, Freund's incomplete adjuvant, and combinations thereof.

In yet another aspect, there is provided a method for the manufacture of the immunogenic composition, comprising:

providing the at least two antigens;
conjugating each of the at least two antigens to a carrier molecule; and
preparing each conjugate at a dose of about 5 μg/dose to about 30 μg/dose.

In some embodiment, the conjugation method for the manufacture of the immunogenic composition is performed by:

carbodiimide mediated modification of the antigen with adipic acid dihydrazide (ADH) introducing reactive hydrazide groups that are then used to link to the carrier molecule via a second carbodiimide step;
derivatization of the antigen with the amine reactive reagent succinimidyl 4-maleimidylbutyrate (GMBS) that introduces a maleimide moiety that is then linked to a reactive sulfhydryl of the derivatized molecule via formation of a thio ether bond; or
CDAP chemistry.

One embodiment of the invention comprises *S. typhi Vi* conjugated by carbodiimide mediated modification of *S. typhi Vi* polysaccharide with adipic acid dihydrazide (ADH) that introduces reactive hydrazide groups that are then used to link to tetanus toxoid (TT) via a second carbodiimide step.

Another embodiment of the invention comprises *S. paratyphi* conjugated via by either 1-cyano-4-dimethylamino-pyridinium tetrafluoroborate (CDAP) chemistry to link *S. enteritidis* core-0 polysaccharide (COPS) to the homologous serovar FliC flagellin protein subunits that had been derivatized with ADH using carbodiimide or by modification at the polysaccharide terminal 2-keto-3-deoxyoctonate (KDO) carbonyl with an aminooxy thiol linker. The aminooxy forms an oxime bond with the KDO ketone that is further reduced with sodium cyanoborohydride.

Another embodiment of the invention comprises *S. typhimurium* FliC protein conjugate derivatized with the amine reactive reagent succinimidyl 4-maleimidylbutyrate (GMBS) to introduce a maleimide moiety that is then linked to the reactive sulfhydryl of the derivatized COPS molecule via formation of a thio ether bond.

Another embodiment of the invention comprises a *S. typhimurium* conjugate component generated by modification at the polysaccharide terminal 2-keto-3-deoxyoctonate (KDO) carbonyl with an aminooxy thiol linker. The aminooxy forms an oxime bond with the KDO ketone that is further reduced with sodium cyanoborohydride. *S. typhimurium* FliC protein is derivatized with the amine reactive reagent succinimidyl 4-maleimidylbutyrate (GMBS) to introduce a maleimide moiety that is then linked to the reactive sulfhydryl of the derivatized COPS molecule via formation of a thioether bond. There is no conjugate vaccine for human use that utilizes the specific method of conjugation employed for *Salmonella typhimurium* glycoconjugate as presented in this disclosure.

Another embodiment of the invention comprises a *S. enteritidis* conjugate generated by 1-cyano-4-dimethylaminopyridinium tetrafluoroborate (CDAP) chemistry to link *S. enteritidis* core-0 polysaccharide (COPS) to the homologous serovar FliC flagellin protein subunits that had been derivatized with ADH using carbodiimide.

In another aspect, there is provided a method for preventing or treating a *Salmonella* infection comprising administering to a patient an effective amount of the immunogenic composition according to embodiments of the present invention. In some embodiment, there is provided a method for preventing or treating a *Salmonella* infection comprising parenteral administration to a patient an effective amount of the immunogenic composition according to embodiments of the present invention. In some embodiments, there is provided a method for preventing or treating a *Salmonella* infection comprising administering to a patient an effective amount of the immunogenic composition according to embodiments of the present invention, wherein administration results in an eight-fold rise in antibody titer.

Another embodiment of the invention is directed to administering a conjugate of the disclosure to a patient. Administration may be for prophylaxis or treatment, and may comprise oral administration, nasal administration, injection such as administration via intravenous, intramuscular, or intraperitoneal, or a combination thereof. In an embodiment administration comprises a single dose, but may comprises multiple doses such as two, three, four or more doses.

The following examples illustrate embodiments of the invention, but should not be viewed as limiting the scope of embodiments of the invention.

EXAMPLES

Example 1: Vaccines Generated

The combined glycol-conjugate vaccine compositions of the present disclosure are provided in Table 1.

TABLE 1

Vaccines according to embodiments of the invention

| Vaccine category | Description |
|---|---|
| Monovalent | *Salmonella paratyphi* A conjugate vaccine (Single dose) 5-30 μg/dose, PBS buffer pH: 6.5-7.5 |
| | *Salmonella paratyphi* A conjugate vaccine (multi dose) 5-30 μg/dose, 2-Phenoxy ethanol, PBS buffer pH: 6.5-7.5 |
| Bivalent | Bivalent conjugate vaccine contains *Salmonella typhi* Vi conjugate and *Salmonella paratyphi* A conjugate (Single dose) 5-30 μg each/dose, PBS buffer with tween 80, pH: 6.5-7.5 |
| | Bivalent conjugate vaccine contains *Salmonella typhi* Vi conjugate and *Salmonella paratyphi* A conjugate (multidose) 5-30 μg each/dose, PBS buffer with tween 80, 2-Phenoxy ethanol, pH: 6.5-7.5 |
| Bivalent | Bivalent conjugate vaccine contains *Salmonella enteritidis* conjugate and *Salmonella typhimurium* conjugate (Single dose) 5-30 μg each/dose, PBS buffer pH: 6.5-7.5 |
| | Bivalent conjugate vaccine contains *Salmonella enteritidis* conjugate and *Salmonella typhimurium* conjugate (multidose) 5-30 μg each/dose, PBS buffer with tween 80, 2-Phenoxy ethanol, pH: 6.5-7.5 |
| Trivalent | Trivalent conjugate vaccine contains *Salmonella typhi* Vi conjugate, *Salmonella enteritidis* conjugate and *Salmonella typhimurium* conjugate (Single dose) 5-30 μg each/dose, PBS buffer pH: 6.5-7.5 |
| | Trivalent conjugate vaccine contains *Salmonella typhi* Vi conjugate, *Salmonella enteritidis* conjugate and *Salmonella typhimurium* conjugate (multidose) 5-30 μg each/dose, PBS buffer with tween 80, 2-Phenoxy ethanol, pH: 6.5-7.5 |
| Tetravalent | Tetravalent conjugate vaccine contains *Salmonella typhi* Vi conjugate, *Salmonella paratyphi* A conjugate, *Salmonella enteritidis* conjugate and *Salmonella typhimurium* conjugate (Single dose) 5-30 μg each/dose, PBS buffer pH: 6.5-7.5 |
| | Tetravalent conjugate vaccine contains *Salmonella typhi* Vi conjugate, *Salmonella paratyphi* A conjugate, *Salmonella enteritidis* conjugate and *Salmonella typhimurium* conjugate (Multi dose) 5-30 μg/dose, PBS buffer with tween 80, 2-Phenoxy ethanol, pH: 6.5-7.5 |
| Combination Meningococcal conjugate vaccine | Meningococcal polysaccharide or glycoconjugate mixed with any of the above monovalent (typhoid), bivalent, tri-valent or tetravalent combination with phenoxy ethanol as preservative. |

Example 2: Methods of Vaccine Generation

A. Preparation of S. *Enteritidis* COPS:FliC Conjugate:

Conjugation of S. *Enteritidis* COPS to S. *Enteritidis* FliC is accomplished with cyanylation chemistry to generate a lattice conjugate that is cross-linked at multiple random COPS hydroxyls to multiple random primary amines and hydrazides on the protein. For this, the protein is first derivatized at protein carboxyls with adipic acid dihydrazide using carbodiimide. Separately, COPS is activated with CDAP to introduce a reactive cyanate group at polysaccharide hydroxyls. The derivatized protein and the activated polysaccharide are then mixed together as the protein and polysaccharide are linked to each other at multiple points; this forms a heterogeneous lattice that varies both in molecular weight and distribution of linkage points. The FIG. 1 shows an overview of the process for chemical synthesis of the *S. enteritidis* COPS:FliC conjugate.

Protein activation: S. *Enteritidis* FliC (stored in 0.9% saline) is concentrated to >6.0 mg/ml and then brought to 0.1% Tween 20, at which point it is confirmed to be monomeric form by HPLC-SEC. If found to be polymeric, it is then subjected to monomerization by lowering to pH 2 for 30 mins at 5±3° C., then raising to pH 7 with NaOH. The FliC is then derivatized with 0.5 M adipic acid dihydrazide (ADH) using 0.5 M ADH in 100 mM MES pH 6.5 by making the solution 5 mg/mL EDC for 17±1 hours at 5±3° C. The FliC-ADH is then diafiltered against 40-diavolumes of borate-buffer pH 9.2 using 10 kDa TFF. Protein ADH labeling and removal of free ADH are confirmed using the TNBS assay prior to proceeding to conjugation.

Polysaccharide activation: S. *Enteritidis* COPS is brought to 10 mg/ml in WFI at 5±3° C. CDAP (100 mg/ml in acetonitrile) is then added at a ratio of 0.5 mg:mg to the dissolved COPS, and incubated for 30 seconds at 5±3° C., at which point 2.5 M DMAP is added to bring the pH to 9.5. After incubation for 6 minutes at 5±3° C., the activated COPS is used immediately for conjugation by adding FliC-ADH.

Conjugation process: Freshly activated COPS-CN is added to FliC-ADH at a 1:1 mg:mg ratio and incubated with continuous stirring for 17±1 hour at 5±3° C. The conjugation reaction is quenched by bringing to 0.2 M Glycine-HCl and stirring for 24 hrs at room temperature.

Purification of DS from unreacted components: The crude conjugate is centrifuged at 4° C., 4000±200 rpm for 15 minutes and the insoluble material pellet is discarded. The cleared supernatant is fractionated in 10 mM PBS using a Superdex 200 PG columns attached to a K-Prime chromatography system. Fractions containing high molecular weight conjugate are analyzed for protein and carbohydrate. Selected qualified fractions are pooled and then concentrated and diafiltered with 10 kDa TFF against 15 diavolumes of 10 mM PBS pH 7.1. The final concentrated COPS: FliC conjugate bulk is sterile filtered through 0.22 μm under sterile conditions and stored at 2-8° C.

Capping of unreacted active groups: Activation of the COPS with CDAP, and FliC with ADH introduces cyanate esters and hydrazide groups, respectively, to these molecules that react with each other during conjugation to form an amide bond. Although this reaction is efficient and robust with chemical linkages consistently formed, a portion of these activated groups remain unreacted during conjugation. In order to quench the residual COPS cyanate esters, an excess of glycine is added to the mixture which reacts with the remaining unreacted cyanate groups and caps them by forming a covalent link to glycine. This capping approach is specific for the cyanate esters, and hence no other changes are expected to occur upon glycine addition. A comparable approach is not readily implementable for quenching unreacted hydrazides, as the reactive group is a primary amine and a quenching reagent would react broadly with primary amines present on the protein amino acid side chains (e.g., lysine) as well, generating neo-epitopes. We have found that during conjugation, many of the hydrazides are consumed by the reaction, some remain uncapped (see report in Appendix VII-9). However, the calculated residual level of <2 μg of ADH per dose is less than the calculated permitted daily exposure for a single administration of 120 μg (see Gadd Toxicology evaluation, Appendix VII-10) does not explicitly cap unreacted hydrazides. This vaccine is licensed and prequalified by WHO and has been administered to hundreds of thousands of adults and children in whom it has been found to be safe and efficacious.

B. Preparation of S. *Typhimurium* COPS:FliC Conjugate:

*S. Typhimurium* COPS is variably 0-acetylated at both the abequose and rhamnose monosaccharides in the OPS repeating unit. In order to preserve the OPS 0-acetyls, S. *Typhimurium* COPS:FliC conjugates are thus synthesized with a method that is conducted at neutral to slightly acidic pH levels. This is accomplished by derivatizing both COPS and FliC with linkers that react with each other to form the conjugate. The KDO carbonyl is modified with an aminooxy-thiol linker that upon reduction with sodium cyanoborohydride generates a sulfhydryl group that is linked to the OPS reducing-end terminus with an oxime bond. The protein is derivatized with GMBS that places thiol-reactive maleimides at protein amino acids with primary amine containing side chains (e.g., lysine). The conjugate is rapidly formed upon mixing of the activated COPS and FliC, generating a "sun-type" conjugate that is linked at multiple FliC sites to the reducing-end of different COPS molecules. The FIG. 2 provides an overview of the process for chemical synthesis of the *S. Typhimurium* COPS:FliC conjugate Polysaccharide activation: S. *Typhimurium* COPS is brought to 10 mg/ml in WFI and derivatized at the polysaccharide reducing end 2-keto-3-deoxyoctonate (KDO) carbonyl with 1:5 mg:mg ratio of an aminooxy thiol linker (O-3-Mercapto-propyl-hydroxyl-amine). In this reaction, the linker aminooxy group forms an oxime bond with the KDO carbonyl. The reaction is incubated at pH 5.3 with gentle stirring for 18±1 hrs at room temperature, at which point the oxime bond is reduced by bringing the mixture to 10 mM sodium cyanoborohydride and incubating for an additional 2.5 hours at room temperature. This mixture is centrifuged at 4000 rpm at 4° C. and supernatant is collected and diafiltered 20-fold against 10 mM PBS 5 mM EDTA 0.1% Tween 20 (pH 6.8) using a 10 kDa TFF membrane to remove unreacted linker prior to use in the conjugation reaction. COPS labeling with the aminooxy thiol linker is confirmed prior to use for conjugation by assessing the thiol:polysaccharide ratio with the resorcinol polysaccharide assay to measure total COPS and the DTNB assay to measure free thiol groups.

Protein activation: S. *Typhimurium* FliC (stored in 0.9% saline) is concentrated to >6.0 mg/ml, confirmed for monomeric form by HPLC-SEC, and then brought to 0.1% Tween 20. If found polymeric then it is subjected to monomerization by lowering to pH 2 for 30 mins at 5±3° C., then rising to pH 7 with NaOH. FliC monomers are brought to 100 mM PBS pH 7.4 and then labeled with the amine reactive reagent succinimidyl 4-maleimidylbutyrate (GMBS) to introduce a maleimide moiety at protein lysines. For this, GMBS is prepared in DMSO, and then added to FliC at a 30:1 molar ratio for 1 hour at room temperature with gentle stirring. The labeled protein is then immediately purified from unreacted linker and solvents with 10 kDa TFF and 10 diavolumes of 10 mM PBS+5 mM EDTA pH 6.8 and used for conjugation to maximize reactivity of the maleimide group that undergoes slow hydrolysis in aqueous solution.

Conjugation Process: The purified COPS-SH is added to FliC-GMBS at a ratio of 2.8:1 mg:mg and incubated at pH 7.4 at room temperature for 12±01 hrs under gentle stirring. The reaction is quenched by addition of 50 mM 2-mercaptoethanol and incubation for 1 hr at RT under stirring. Thiol-labeled COPS and maleimide-labeled FliC are mixed at a ratio of 2.8:1 COPS-thiol:FliC-maleimide and incubated for 12-18 hours at 2-8° C. with gentle mixing.

Purification of DS from unreacted components: The crude conjugate is centrifuged at 4° C. at 4000±200 rpm for 15 mins and the insoluble material pellet is discarded. The cleared supernatant is fractionated in 10 mM PBS using a Superdex 200G columns attached to a K-Prime chromatography system. Fractions containing high molecular weight conjugate are analyzed and selected for pooling. Selected qualified fractions are pooled, and then concentrated and diafiltered by 10 kDa TFF against 15 diavolumes of 10 mM PBS pH 7.1. The final concentrated COPS:FliC conjugate bulk is sterile filtered through 0.22 μm under sterile conditions and stored at 2-8° C.

Capping of unreacted active groups: The aminooxy-thiol linker used for COPS derivatization is a hetero-bifunctional linker with unique groups (aminooxy and sulfhydryl) at either end. When the aminooxy group reacts with the COPS (Carbonyl on KDO) this caps the aminooxy functionality, and the unreacted linker is removed from the labeled COPS. Thus, in the absence of free linker, the aminooxy groups are considered to be capped by COPS. Linkage of the sulfhydryl present at the end of the aminooxy-thiol labeled COPS obligate capping of the active group. Any remaining uncapped thiols are thus inherently associated with unlinked free OPS. The FliC protein is decorated with maleimide groups following modification with GMBS. Residual unreacted GMBS linker is removed by TFF filtration. Maleimides are unstable at neutral pH, and rapidly hydrolyze; hence the labeled/activated polysaccharide is rapidly added following FliC derivatization in order to maximize conjugation efficiency. In order to cap any possible unreacted maleimides that may remain during conjugation, a molar excess of β-mercaptoethanol (βME) is added whereby the βME sulfhydryls react with the remaining active maleimide groups, functionally extinguishing their activity.

C. Preparation of *S. Typhi* ViPs-TT Conjugate (Typbar-TCV™)

Typbar-TCV™ is comprised by the purified Vi capsule polysaccharide of S. *Typhi* linked to tetanus toxoid. Synthesis of the conjugate is accomplished by first derivatizing Vi with ADH at the polysaccharide carboxyl groups with carbodiimide chemistry, followed by then linking the ADH derivatized Vi to tetanus toxoid carboxyls with same carbodiimide approach. The FIG. 3 shows an overview of the process for chemical synthesis of S. TyphiVi-TT (Typbar-TCV™) conjugate.

Polysaccharide activation: S. *Typhi* Vi PS bulk (stored at −20° C.) is thawed at room temperature. Hydrolysis of the bulk to partially de-O-acetylate Vi is performed by addition of 0.45 M sodium carbonate and bicarbonate buffer under gentle stirring for 15 minutes at 2-8° C., after which the pH is adjusted to 7 using 50% glacial acetic acid and the material is then buffer exchanged at RT against 0.1 M MES/50 mM NaCl pH 6(MES buffer) with 30 kDa TFF. The partially de-O-acetylated bulk is then treated with ADH and EDC for 4 hours at 2-8° C. to label the carboxylic acid groups with ADH. The activated polysaccharide is then buffer exchanged and concentrated first against PBS, and then MES buffer using 300 kDa TFF.

Conjugation process: The Tetanus Toxoid bulk is buffer exchanged and concentrated against MES buffer pH 5.8 with 30 kDa TFF. The ADH-derivatized Vi and Tetanus Toxoid bulks are then mixed at a 1:1 mg:mg ratio, in the presence of EDC at 2-8° C., and mixed with gentle stirring until viscosity of the conjugate bulk reaches a specified viscosity limit (cP), whereupon the reaction is quenched by adjusting pH to 7.4 slowly by adding 20 mM EDTA pH 8.5 under stirring for 10-15 minutes.

Purification of DS from unreacted components: The quenched Vi:TT is purified by 1,000 kDa TFF with 10 diavolumes of 10 mM MES, 50 mM NaCl, pH 6.0 and then 10 diavolumes of 10 mM PBS pH 7.1. This process is sufficient to remove free Vi and protein to levels below 20% and 1% respectively. The final purified conjugate bulk is sterile filtered through 0.22 μm filter under sterile conditions and stored at 2-8° C. pending QC approval.

Capping of unreacted active groups: Vi is modified in a limiting fashion with ADH, and following addition of an excess of TT protein, the hydrazide groups on the activated Vi are effectively capped. It was found that the remaining level of uncapped hydrazide in Typbar-TCV™ is indeed very low, presumably due to factors including: i.) derivatization with ADH is under sub-saturating conditions (i.e., few hydrazides per molecule) and ii.) an excess of TT is added to the conjugation reaction, thus the molar ratio of protein carboxyls available for conjugation is in excess to the polysaccharide hydrazides.

Studies were performed to evaluate the potential local and systemic toxicity and the persistence or reversibility of any effects during a 14-day treatment free period of bivalent conjugate vaccine (containing *Salmonella enteritidis* and *S. typhimurium* vaccines comprised of Core-O polysaccharide [COPS] conjugated for phase 1 flagellin [MC]), and trivalent conjugate vaccine (containing *S. Enteritidis* and *S. Typhimurium* COPS:FliC conjugate vaccines and *S. typhi* Vi conjugate vaccine [Typbar-TCV™]) when administered by intramuscular injection to male and female New Zealand White rabbits.

All animals survived to scheduled termination. There were no test article-related adverse changes in mortality, clinical observations, physical exams, injection site scores, body weights, food consumption, organ weights, organ to body weight ratios, body temperature, ophthalmology or urinalysis.

Following administration of the vaccine boosts, test article groups exhibited changes in clinical pathology and histopathology indicative of an acute inflammatory response.

Pathological changes at Day 86/87 in the test article groups included inflammatory lesions at the injection sites, consisting microscopically of heterophilic and/or mixed cell inflammation of the dermis, subcutis and/or muscle and myocyte necrosis or degeneration. Inflammatory cells were present in the medullary sinuses of the draining iliac lymph nodes as an indirect effect of the inflammation observed at the injection sites. The reactions were more prevalent and/or severe on the left side as a result of the Day 85 dose. Overall the trivalent multiple dose vaccine group (Group 4), was mildly more affected in severity than bivalent vaccine dose groups. Unlike bivalent groups, Group 4 females were observed to have inflammation at injection sites in both the right (last injection Day 57) and left side (last injection Day 85).

Additional indicators of an acute inflammatory reaction in the test article dosed groups included increased neutrophil and monocyte counts on Day 86/87 and higher fibrinogen and C-Reactive Protein concentrations on Days 3 and 86/87 following dosing on Days 1 and 85.

These changes were not present at the recovery sacrifice on Day 99/100 indicating the resolution of the inflammation during the 14-day post-dose period.

Example 3: Serological Analysis of Vaccines

Both bivalent and trivalent formulations were subjected for toxicity studies whereas only trivalent vaccine alone was taken forward for immunogenicity studies. Both bivalent and Trivalent formulations were designed with the same buffer constituents and same strengths of individual antigens. For evaluating immunogenicity studies, only trivalent formulation was chosen the reason being that that the trivalent formulation covers the components of bivalent formulation. The results indicated that the trivalent formulation has given high fold rise of antibodies by which it is expected that the bivalent as a separate vaccine should also express the same level of immunogenicity for the respective diseases.

Immunogenicity Studies of the Trivalent *Salmonella* Conjugate Vaccine Drug Product:

The trivalent *Salmonella* conjugate vaccine drug product in multi-dose vials and the bivalent *Salmonella* conjugate vaccine drug product in both multi-dose and mono-dose vials were maintained in controlled storage at 2-8° C. with stability being monitored only for the Vi conjugate component because qualified assays were not available during 21 months for monitoring the *S. enteritidis* and *S. typhimurium* components.

Embodiments of the invention describe a methodology to monitor the components of the trivalent and bivalent conjugate vaccines. This was accomplished by measuring total COPS by resorcinol (which is not affected by the Vi capsular polysaccharide). The *S. typhimurium* COPS is then measured by an inhibition ELISA using a potent monoclonal antibody specific for the immunodominant antigen 4 of Group B *Salmonella*; since serovar *S. typhimurium* is a member of Group B *Salmonella*, it reacts with this monoclonal antibody. The *S. typhimurium* COPS value is then subtracted from the total resorcinol COPS value to provide a quantification of the *S. enteritidis* COPS. This test was effective in measuring both total COPS and free (unconjugated) COPS.

The resorcinol subtraction method has proved to be a reliable method. Two studies of rabbit immunogenicity were performed in which animals were vaccinated with a single dose of trivalent *Salmonella* conjugate vaccine to assess the immunogenicity of the vaccine components 7 months and 8 months after 20 rabbits had been vaccinated in the rabbit toxicology study with the same trivalent *Salmonella* conjugate vaccine. The doses of trivalent conjugate vaccine came from the remaining vials of vaccine that were stored at 2-8° C. under GLP (Good Laboratory Practices) conditions at CRO that performed the rabbit toxicology study. In total, results from three separate rabbit immunogenicity studies spread over 8 months were obtained that provided data for monitoring the immunogenicity of the trivalent *salmonella* conjugate vaccine. The design and features of the rabbit immunogenicity studies are described below in Table 2.

Rabbit Toxicology Study—Analysis of the antibody titers from Group 4 of the rabbit toxicology study performed from the 20 rabbits that received the trivalent *Salmonella* conjugate vaccine, documenting the immunogenicity of the trivalent *Salmonella* conjugate vaccine when it was 14 months from time of release. In particular, the results show the immunogenicity four weeks after administration of the first dose of the trivalent conjugate (assessed by comparing the day 1 and day 29 antibody titers), thereby providing evidence of the immune response following a single dose of the trivalent *Salmonella* conjugate vaccine.

Rabbit Immunogenicity Study #1—An immunogenicity study in which 10 rabbits were given a single dose of trivalent conjugate vaccine and blood was drawn on day 1 (the day of immunization) and four weeks later (day 29). Paired sera were available from nine rabbits.

Rabbit Immunogenicity Study #2—A second smaller immunogenicity study was carried out 6 weeks after animals in Rabbit Immunogenicity Study #1 were vaccinated. Five rabbits, all female, were immunized with a single dose from the last final remaining vial of trivalent *Salmonella* conjugate vaccine.

Methods—the 10 rabbits that were utilized in Rabbit Immunogenicity Study #1 (yielding paired sera from nine animals) and the five rabbits utilized in Rabbit Immunogenicity Study #2 (yielding paired sera from all five rabbits) were all Special Pathogen Free (SPF) juvenile animals of the same variety (New Zealand White), age (10-16 weeks at time of dosing) and weight (>2.2 kg), and obtained from the same vendor (Charles River Laboratories), as the rabbits that were used in the Rabbit Toxicology Study. All rabbits were acclimated for at least 7 days prior to dosing. The serum specimens were collected on the identical time points, day 1 and day 29, as in the larger (20-animal) Rabbit Toxicology Study. Sera from all three studies were tested by the identical serological assay (IgG ELISA), using the identical source of *S. enteritidis* COPS, *S. typhimurium* COPS and *S. typhi* Vi antigens. Thus, methods and animals were standardized across all three immunogenicity studies to minimize sources of variability.

TABLE 2

Summary of antibody responses to *Enteritidis* COPS, *Typhimurium* COPS and *Typhi* Vi from rabbits immunized with a single dose of Trivalent *Salmonella* Conjugate Vaccine in three separate studies performed over a period of 8 months

| TOXICOLOGY STUDY, GROUP 4* *S. Enteritidis* COPS IgG (EU/ml) | | | | | IMMUNOGENICITY STUDY #1 *S. Enteritidis* COPS IgG (EU/ml) | | | | | IMMUNOGENICITY STUDY #2 *S. Enteritidis* COPS IgG (EU/ml) | | | | |
|---|---|---|---|---|---|---|---|---|---|---|---|---|---|---|
| No. of rabbits | Sex | 0 day | $29^{th}$ day | Fold-rise | No. of rabbits | Sex | 0 day | $29^{th}$ day | Fold-rise | No. of rabbits | Sex | 0 day | $29^{th}$ day | Fold-rise |
| 20 | 10 F, 10 M | | | day 29 over day 1 | 9** | 5 F, 4 M | | | day 29 over day 1 | 5 | 5 F | | | day 29 over day 1 |
| >4-fold rises n/N (%) | | | | 20/20 (100%) | | | | | 9/9 (100%) | | | | | 5/5 (100%) |
| Geometric mean | | 7.2 | 4,381.4 | 610.8 | Geometric mean | | 3.0 | 1,849.6 | 651.4 | Geometric mean | | 3.3 | 1,143.5 | 346.7 |
| Minimum | | 2.5 | 1,171.4 | 75.6 | Minimum | | 2.5 | 138.6 | 12.2 | Minimum | | 2.5 | 128.4 | 51.4 |
| Maximum | | 54.7 | 10,677.8 | 3,202.8 | Maximum | | 11.4 | 7,702.6 | 3,081.0 | Maximum | | 5.0 | 10,991.5 | 4,396.6 |
| TOXICOLOGY STUDY, GROUP 4* *S. Typhimurium* COPS IgG (EU/ml) | | | | | IMMUNOGENICITY STUDY #1 *S. Typhimurium* COPS IgG (EU/ml) | | | | | IMMUNOGENICITY STUDY #2 *S. Typhimurium* COPS IgG (EU/ml) | | | | |
| No. of rabbits | Sex | 0 day | $29^{th}$ day | Fold-rise | No. of rabbits | Sex | 0 day | $29^{th}$ day | Fold-rise | No. of rabbits | Sex | 0 day | $29^{th}$ day | Fold-rise |
| 20 | 10 F, 10 M | | | day 29 over day 1 | 9** | 5 F, 4 M | | | day 29 over day 1 | 5 | 5 F | | | day 29 over day 1 |

TABLE 2-continued

Summary of antibody responses to *Enteritidis* COPS, *Typhimurium* COPS and *Typhi* Vi from rabbits immunized with a single dose of Trivalent *Salmonella* Conjugate Vaccine in three separate studies performed over a period of 8 months

| | | | | | | | | | | | |
|---|---|---|---|---|---|---|---|---|---|---|---|
| >4-fold rises n/N (%) | | | 20/20 (100%) | >4-fold rises n/N (%) | | | 9/9 (100%) | >4-fold rises n/N (%) | | | 5/5 (100%) |
| Geometric mean | 3.2 | 1,454.2 | 426.9 | Geometric mean | 3.1 | 1,849.6 | 621.4 | Geometric mean | 3.3 | 404.5 | 77.4 |
| Minimum | 2.5 | 102.5 | 41.0 | Minimum | 2.5 | 138.6 | 37.9 | Minimum | 2.5 | 23.9 | 9.6 |
| Maximum | 15.7 | 17,442.8 | 6,977.1 | Maximum | 9.5 | 15,793.5 | 1,662.4 | Maximum | 5.0 | 3,627.9 | 1,451.2 |

| TOXICOLOGY STUDY, GROUP 4* *S. Typhi* Vi IgG (EU/ml) | | | | | IMMUNOGENICITY STUDY #1 *S. Typhi* Vi IgG (EU/ml) | | | | | IMMUNOGENICITY STUDY #2 *S. Typhi* Vi IgG (EU/ml) | | | | |
|---|---|---|---|---|---|---|---|---|---|---|---|---|---|---|
| No. of rabbits | Sex | 0 day | 29th day | Fold-rise | No. of rabbits | Sex | 0 day | 29th day | Fold-rise | No. of rabbits | Sex | 0 day | 29th day | Fold-rise |
| 20 | 10 F, 10 M | | | day 29 over day 1 | 9** | 5 F, 4 M | | | day 29 over day 1 | 5 | 5 F | | | day 29 over day 1 |
| >4-fold rises n/N (%) | | | | 20/20 (100%) | >4-fold rises n/N (%) | | | | 9/9 (100%) | >4-fold rises n/N (%) | | | | 5/5 (100%) |
| Geometric mean | | 24.0 | 2,409.4 | 100.2 | Geometric mean | | 14.4 | 742.1 | 51.7 | Geometric mean | | 17.0 | 247.5 | 20.7 |
| Minimum | | 5.0 | 774.0 | 12.5 | Minimum | | 5.0 | 234.8 | 7.3 | Minimum | | 14.6 | 153.4 | 9.2 |
| Maximum | | 86.8 | 10,674.3 | 337.4 | Maximum | | 47.3 | 13,161.0 | 1,134.6 | Maximum | | 22.3 | 568.6 | 130.3 |

*Rabbits in the Toxicology Study received four doses of Trivalent *Salmonella* Conjugate Vaccine at an interval of 4 weeks between doses. These data show the antibody responses following the first dose of Trivalent vaccine.

**10 rabbits were immunized on day 1. 1 male rabbit died before day 29 (unrelated to study product), so paired sera were available for only 9 rabbits in this study Results—Table 2 summarizes the serological results from the three sets of rabbits immunized with a single dose of trivalent *Salmonella* conjugate vaccine (Toxicology Study; N=20 rabbits), Immunogenicity Study #1; (N=9 rabbits) [with paired serum specimens]) and (N=5 rabbits). Serological data from these three time points provide an opportunity to establish whether or not the three different conjugate vaccines within the trivalent *Salmonella* conjugate vaccine remain comparably immunogenic over several months or whether there is evidence of an important fall in titers to one or another component conjugate.

Within each individual study, the fold-rise in titer of each rabbit to each of the three vaccine antigens (*S. enteritidis* COPS, *S. typhimurium* COPS and *S. typhi* Vi) is the key measurement.

The four key parameters to be compared across the studies should be:

i) Percent of rabbits demonstrating a >4-fold rise in titer among the total rabbits immunized.

ii) Geometric Mean Fold-Rise in titer iii) Minimum fold-rise in titer iv) Maximum fold-rise in titer Conclusions from Analysis of the Serological Data:

The Rabbit Toxicology Study results with 20 rabbits (10 female, 10 male) and the Immunogenicity Study #1 with 9 rabbits (5 female, 4 male) provide a reasonable N (No. of animals) per study for comparison. Comparing the Geometric Mean Fold-Rise in titer and the minimum and maximum rise in titer for each of the three antibodies (anti-*enteritidis* COPS, anti-*typhimurium* COPS and anti-Vi PS) from the Rabbit Toxicology Study and Immunogenicity Study #1, each individual conjugate in the trivalent conjugate vaccine is seen to have retained its ability to stimulate serum antibodies, despite a difference of 7 months in the age of the drug product when used in the two studies.

In comparing serological results from Immunogenicity Study #2 with Immunogenicity Study #1 and with results of the Rabbit Toxicology Study, all three conjugates elicited at least a four-fold rise in titer to each vaccine antigen in each rabbit. Indeed, all but one rabbit exhibited a >8-fold rise in titer to each vaccine antigen. Thus, the *Salmonella* trivalent conjugate vaccine remained immunogenic. The Geometric Mean Fold Rise was somewhat lower for *S. typhimurium* and Vi antibodies in the small rabbit Immunogenicity Study #2. However, the minimum fold rise in titer and the maximum fold rise in titer were similar to those recorded in the Rabbit Toxicology Study and in Immunogenicity Study #1. This suggests that the difference in Geometric Mean Fold-Rise is due to the small numbers, particularly in Rabbit Immunogenicity Study #2.

The fold-rise in titer for each group of animals for each antibody assay was compared by Wilcoxon Rank Sum to determine if the fold rises in the 20 rabbits in the Toxicology Test were significantly different ($p<0.05$) for any of the three antibodies from the fold-rises of the nine rabbits in Immunogenicity Test #1. There were no significant differences. The same statistical test (Wilcoxon Rank Sum) was conducted to compare fold rises between day 1 and day 29 for each antibody comparing the nine rabbits in Immunogenicity Study #1 with the 5 rabbits in Immunogenicity Study #2. No significant differences were observed.

Example 4: Description of Testing

Controlled experiments were conducted as described in Table 3.

TABLE 3

| Test and Control Article Identification | |
|---|---|
| Test Article: | Bivalent Vaccine |
| Identification: | Bivalent Vaccine, Single dose vial; no preservative |
| Dose/ Concentration: | 50 μg/dose (25 μg *S. enteritidis* COPS:FliC + 25 μg *S. typhimurium* COPS:FliC) |
| Storage Temperature: | 2 to 8° C. |
| Other: | Bivalent vaccine contains *S. enteritidis* and *S. typhimurium* COPS:FliC conjugate vaccines |
| Test Article: | Bivalent Vaccine |
| Identification: | Bivalent Vaccine, Multiple dose vial with 2-phenoxyethanol preservative |
| Dose/ Concentration: | 50 μg/dose (25 μg *S. enteritidis* COPS:FliC + 25 μg *S. typhimurium* COPS:FliC) |
| Storage Temperature: | 2 to 8° C. |
| Other: | Bivalent vaccine contains *S. enteritidis* and *S. typhimurium* COPS:FliC conjugate vaccines |
| Test Article: | Trivalent Vaccine |
| Identification: | Trivalent Vaccine, Multiple dose vial with 2-phenoxyethanol preservative |
| Dose/ Concentration: | 75 μg/dose (25 μg *S. enteritidis* COPS:FliC + 25 μg *S. typhimurium* COPS:FliC + 25 μg *S. typhi* Vi conjugate [Typbar-TCV ™]) |
| Storage Temperature: | 2 to 8° C. |
| Other: | Trivalent vaccine contains *S. enteritidis* and *S. typhimurium* COPS:FliC conjugate vaccines and *S. typhi* Vi conjugate vaccine [Typbar-TCV ™] |
| Control Article: | Vehicle/Control Article |
| Identification: | Formulation Buffer containing 2-phenoxyethanol |
| Dose/ Concentration: | 0 μg/dose (500 μl volume/dose) |
| Storage Temperature: | 2 to 8° C. |
| Storage Location: | Test Article Storage |
| Other: | Placebo (Tween-80, 2-PE and PBS) for Multi Dose |

Example 5 Experimental Design

Eighty (80) rabbits (40/sex) were divided into four (4) groups of twenty (20) animals (10/sex/group). See Table 2 for group description, test/control article administration, and necropsy days. The procedures followed are listed in Table 4.

TABLE 4

Study Group Descriptions

| Group | Test Article | Test Article Dose/ Rabbit (μg/dose) | Type of Vial | Number of Animals: Main Phase Males | Main Phase Females | Recovery Phase Males | Recovery Phase Females |
|---|---|---|---|---|---|---|---|
| 1 | Formulation Buffer with preservative | 0 | Multiple dose | 5 | 5 | 5 | 5 |
| 2 | Bivalent[a] | 50 | Single dose; no preservative | 5 | 5 | 5 | 5 |

TABLE 4-continued

| Study Group Descriptions | | | | | | | |
|---|---|---|---|---|---|---|---|
| | | Test Article Dose/ Rabbit | | Number of Animals | | | |
| | | | | Main Phase | | Recovery Phase | |
| Group | Test Article | (μg/dose) | Type of Vial | Males | Females | Males | Females |
| 3 | Bivalent[a] | 50 | Multiple dose with preservative | 5 | 5 | 5 | 5 |
| 4 | Trivalent[b] | 75 | Multiple dose with preservative | 5 | 5 | 5 | 5 |

[a]Bivalent vaccine contains *S. enteritidis* and *S. typhimurium* COPS:FliC conjugate vaccines.
[b]Trivalent vaccine contains *S. enteritidis* and *S. typhimurium* COPS:FliC conjugate vaccines and *S. typhi* Vi conjugate vaccine [Tybar-TCV ™].

Example 6: Results

The mean C reactive protein (CRP concentrations increased markedly and statistically significantly in vaccine-dosed groups on Days 3 and 86/87, relative to dosing on Day 1 or 85, respectively, indicating acute inflammation. The higher values on Day 86/87 correlated with the aforementioned microscopic observation of inflammation primarily at the injection site at terminal necropsy. With the exception of one control male, the CRP values were well below 32 μg/mL in all control and vaccine-dosed animals by Day 99/100, indicating the reversibility of this change. CRP values were statistically significantly different compared to control animals (see Table 5).

TABLE 5

| Summary of CRP Statistics | | | | | | | | | | | | | | | | |
|---|---|---|---|---|---|---|---|---|---|---|---|---|---|---|---|---|
| | | D 1 Group | | | D 3 Group | | | D 85 Group | | | D 86-87 Group | | | D 99-100 Group | | |
| Parameter | Sex | 2 | 3 | 4 | 2 | 3 | 4 | 2 | 3 | 4 | 2 | 3 | 4 | 2 | 3 | 4 |
| CRP | F | ns | ns | ns | ↑* | ↑*** | ↑* | ns | ns | ns | ↑*** | ↑*** | ↑*** | ns | ns | ns |
| | M | ns | ns | ns | ↑** | ↑*** | ↑* | ns | ns | ns | ↑*** | ↑*** | ↑*** | ns | ns | ns |

ns = not statistically significant.
↑ = group mean is statistically significantly greater than the control group mean at p < 0.050.
↓ = group mean is statistically significantly less than the control group mean at p < 0.050.
Statistical key: All statistical comparisons made against Group 1 controls for each sex, *p < 0.05, p < 0.01, *p < 0.001

TABLE 6

| Incidence and Mean Severity of Findings at Injection Sites and Inguinal Lymph Nodes at the Day 86 and 87 Sacrifices | | | | | | | | |
|---|---|---|---|---|---|---|---|---|
| | Group | | | | | | | |
| | 1 | | 2 | | 3 | | 4 | |
| | Sex | | | | | | | |
| | M | F | M | F | M | F | M | F |
| | Number | | | | | | | |
| | 5 | 5 | 5 | 5 | 5 | 5 | 5 | 5 |
| Injection Site, Left | | | | | | | | |
| Inflammation, heterophilic or mixed, dermis | — | — | — | — | — | — | 1(2.0) | 1(2.0) |
| Inflammation, heterophilic or mixed, subcutis | — | — | 2(1.5) | 4(1.0) | 2(1.0) | 4(1.3) | 1(1.0) | 1(2.0) |
| Inflammation, heterophilic or mixed, skeletal muscle | — | — | 2(1.5) | — | 1(2.0) | 1(2.0) | 1(3.0) | 1(2.0) |
| Necrosis, myocyte, skeletal muscle | — | — | 1(1.0) | — | — | — | 1(2.0) | 1(3.0) |
| Hemorrhage, subcutis | — | — | 1(1.0) | — | — | — | 1(2.0) | — |

TABLE 6-continued

Incidence and Mean Severity of Findings at Injection Sites and Inguinal Lymph Nodes at the Day 86 and 87 Sacrifices

| | Group 1 | | Group 2 | | Group 3 | | Group 4 | |
|---|---|---|---|---|---|---|---|---|
| Sex | M | F | M | F | M | F | M | F |
| Number | 5 | 5 | 5 | 5 | 5 | 5 | 5 | 5 |
| Hemorrhage, skeletal muscle | — | — | — | — | — | 1(1.0) | 1(3.0) | — |
| Degeneration, myocyte, skeletal muscle | — | — | — | — | 1(1.0) | — | — | — |
| Total Number of Findings | 0 | 0 | 6 | 4 | 4 | 6 | 6 | 4 |
| Injection Site, Right | | | | | | | | |
| Inflammation, heterophilic or mixed, subcutis | — | — | — | — | — | — | — | 2(1.0) |
| Total Number of Findings | 0 | 0 | 0 | 0 | 0 | 0 | 0 | 2 |
| Iliac lymph node, Left | | | | | | | | |
| Sinus heterophils | — | — | 3(1.7) | 1(1.0) | 3(1.7) | 4(1.5) | 2(2.0) | 4(1.5) |
| Total Number of Findings | 0 | 0 | 3 | 1 | 3 | 4 | 2 | 4 |
| Iliac lymph node, Right | | | | | | | | |
| Sinus heterophils | — | — | 2(1.0) | 2(1.5) | 11.0) | — | 1(2.0) | 3(2.0) |
| Total Number of Findings | 0 | 0 | 2 | 2 | 1 | 0 | 1 | 3 |

— = no finding
( ) = sum of severity scores divided by the number of animals affected.

Example 7: Stability Studies

The immunogenic compositions according to embodiments of the invention were subjected to various stability studies. Real-time stability testing was carried for evaluating the stability of vaccine compositions according to embodiments of the invention at recommended storage conditions of 2-8° C.

A. Real Time Stability Study for Bivalent Vaccine of *S. Enteritidis* and *S. Typhimurium Conjugates*

Product Name: Bivalent Vaccine of *S. Enteritidis* and *S. Typhimurium* Conjugates Storage Conditions: 5° C.±3° C.

Stability Study Type: Real Time Stability Study

Pack: 3.0 mL Glass vial

Presentation: 2.5 mL

Dose size: 0.5 mL

Analysis Results: Shown in Table 7

TABLE 7

Real Time Stability Study for Bivalent Vaccine of *S. Enteritidis* and *S. Typhimurium* Conjugates when stored at 5° C. ± 3° C.

| | Spec. | | | | | | | |
|---|---|---|---|---|---|---|---|---|
| Time Point | Description Clear to slightly turbid | pH 6.50-7.50 | *S. Typhimurium* COPS Content For information only | *S. Enteritidis* COPS Content For information only | Total Protein Content For information only | HPLC For information only | *S. Typhimurium* Free COPS Content For information only | *S. Enteritidis* Free COPS Content For information only |
| Zero day | Clear Liquid | 7.13 | 26.6 μg/dose | 25.3 μg/dose | 0.159 mg/mL | Complies | 4.9% | Not detected |
| 3 M (I) | Clear Liquid | 7.18 | Not done | Not done | 0.225 mg/mL | Complies | Not done | Not done |

TABLE 7-continued

Real Time Stability Study for Bivalent Vaccine of *S. Enteritidis* and *S. Typhimurium* Conjugates when stored at 5° C. ± 3° C.

| | Spec. | | | | | | | |
|---|---|---|---|---|---|---|---|---|
| Time Point | Description Clear to slightly turbid | pH 6.50-7.50 | *S. Typhimurium* COPS Content For information only | *S. Enteritidis* COPS Content For information only | Total Protein Content For information only | HPLC For information only | *S. Typhimurium* Free COPS Content For information only | *S. Enteritidis* Free COPS Content For information only |
| 6 M (U) | Clear Liquid | 7.12 | Not done | Not done | 0.175 mg/mL | Complies | Not done | Not done |
| 9 M (I) | Clear Liquid | 7.08 | Not done | Not done | 0.184 mg/mL | Complies | Not done | Not done |
| 12 M (U) | Clear Liquid | 7.01 | Not done | Not done | 0.192 mg/mL | Complies | Not done | Not done |
| 17 M (U) | Clear Liquid | 7.13 | 28.7 μg/dose | 31.6 μg/dose | 0.229 mg/mL | Complies | 28.3% | 35.8% |
| 18 M (I) | Clear Liquid | 7.05 | 31.66 μg/dose | 25.50 μg/dose | 0.209 mg/mL | Complies | 29.07% | 47.32% |
| 19 M (U) | Clear Liquid | 7.12 | 34.34 μg/dose | 23.06 μg/dose | 0.209 mg/mL | Complies | 34.44% | 40.53% |
| 20 M | Clear Liquid | 7.09 | 31.88 μg/dose | 25.41 μg/dose | 0.201 mg/mL | Complies | 34.31% | 40.39% |
| 21 M | Clear Liquid | 7.21 | 34.99 μg/dose | 23.63 μg/dose | 0.205 mg/mL | Complies | 36.77% | 41.38% |
| 22 M | Clear Liquid | 7.15 | 35.36 μg/dose | 23.99 μg/dose | 0.195 mg/mL | Complies | 32.16% | 43.42% |

B. Real Time Stability Study for Trivalent Vaccine of *S. Enteritidis, S. Typhimurium* and *S. Typhi Vi Conjugates*

Product Name: Trivalent Vaccine of *S. Enteritidis, S. Typhimurium S. Typhi* Vi Conjugates Storage Conditions: 5° C.±3° C.

Stability Study Type: Real Time Stability Study

Pack: 3.0 mL Glass vial

Presentation: 2.5 mL

Dose size: 0.5 mL

Analysis Results: Shown in Table 8

TABLE 8

Real Time Stability Study for Trivalent Vaccine of *S. Enteritidis*, *S. Typhimurium* and *S. Typhi* Vi Conjugates when stored at 5° C. ± 3° C.

| | Spec. | | | | | |
|---|---|---|---|---|---|---|
| Time Point | Description Clear to slightly turbid | pH 6.50-7.50 | *S. Typhimurium* COPS Content FIO | *S. Enteritidis* COPS Content FIO | *S. Typhi* Vi Content FIO | Total Protein Content FIO |
| Zero day | Clear Liquid | 7.14 | 25.8 μg/dose | 21.7 μg/dose | 27.0 μg/dose | 0.212 mg/mL |
| 3 M (I) | Clear Liquid | 7.26 | Not done | Not done | 26.4 μg/dose | 0.137 mg/mL |
| 6 M (U) | Clear Liquid | 7.10 | Not done | Not done | 27.2 μg/dose | 0.167 mg/mL |
| 9 M (I) | Clear Liquid | 7.05 | Not done | Not done | 28.1 μg/dose | 0.148 mg/mL |
| 12 M (U) | Clear Liquid | 7.14 | Not done | Not done | 29.0 μg/dose | 0.152 mg/mL |
| 17 M (U) | Clear Liquid | 7.13 | 33.8 μg/dose | 39.5 μg/dose | 26.4 μg/dose | 0.137 mg/mL |
| 18 M | Clear Liquid | 7.15 | 35.2 μg/dose | 37.7 μg/dose | 26.0 μg/dose | 0.142 mg/mL |
| 19 M (U) | Clear Liquid | 7.14 | 36.85 μg/dose | 36.16 μg/dose | 26.1 μg/dose | 0.142 mg/mL |
| 20 M | Clear Liquid | 7.16 | 34.37 μg/dose | 38.75 μg/dose | 26.7 μg/dose | 0.151 mg/mL |
| 21 M | Clear Liquid | 7.09 | 37.80 μg/dose | 32.58 μg/dose | 26.1 μg/dose | 0.128 mg/mL |
| 22 M | Clear Liquid | 7.12 | 39.80 μg/dose | 34.62 μg/dose | 26.4 μg/dose | 0.131 mg/mL |

TABLE 8-continued

Real Time Stability Study for Trivalent Vaccine of *S. Enteritidis*, *S. Typhimurium* and *S. Typhi* Vi Conjugates when stored at 5° C. ± 3° C.

| | Spec. | | | |
|---|---|---|---|---|
| Time Point | HPLC FIO | *S. Typhimurium* Free COPS Content FIO | *S. Enteritidis* Free COPS Content FIO | *S. Typhi* Free Vi Content FIO |
| Zero day | Complies | 14.7% | Not detected | 5.4% |
| 3 M (I) | Complies | Not done | Not done | 5.7% |
| 6 M (U) | Complies | Not done | Not done | 6.2% |
| 9 M (I) | Complies | Not done | Not done | 7.5% |
| 12 M (U) | Complies | Not done | Not done | 8.3% |
| 17 M (U) | Complies | 26.5% | 18.3% | 10.5% |
| 18 M | Complies | 26.0% | 22.1% | 10.9% |
| 19 M (U) | Complies | 23.57% | 24.25% | 10.9% |
| 20 M | Complies | 22.16% | 25.48% | 13.6% |
| 21 M | Complies | 28.99% | 26.12% | 11.8% |
| 22 M | Complies | 29.98% | 26.88% | 13.2% |

FIO: For Information Only

Thus, compositions according to embodiments of the invention were found to be stable at recommended storage conditions of 2-8° C.

Although the invention has been illustrated and described in greater detail with reference to the preferred exemplary embodiments, the invention is not limited to the examples disclosed, and further variations can be inferred by a person skilled in the art, without departing from the scope of protection of the invention.

For the sake of clarity, it is to be understood that the use of "a" or "an" throughout this application does not exclude a plurality, and "comprising" does not exclude other steps or elements.

We claim:

1. An immunogenic composition consisting of a) a bivalent or trivalent antigenic component or b) the bivalent or trivalent antigenic component and an excipient and/or at least one pharmaceutically acceptable substance, wherein said bivalent or trivalent antigenic component is selected from the group consisting of:

(i) an antigen of *Salmonella enteritidis* and an antigen of *Salmonella typhi;*

(ii) an antigen of *Salmonella typhimurium* and an antigen of *Salmonella typhi*; and (iii) an antigen of *Salmonella typhimurium*, an antigen of *Salmonella typhi*, and an antigen of *Salmonella* paratyphi, wherein the antigen of *Salmonella enteritidis* is COPS (core O polysaccharide), the antigen of *Salmonella typhimurium* is COPS and the antigen of *Salmonella typhi* is Vi polysaccharide and the antigen of *Salmonella* paratyphi is COPS, and wherein, each antigen of the antigenic components is conjugated to one or more carrier molecules.

2. The immunogenic composition as claimed in claim 1, wherein each antigen of each bivalent or trivalent antigenic component is at a dose range of about 5 μg/dose to about 30 μg/dose.

3. A method of preventing or treating an illness caused by *Salmonella* infection comprising administering an effective amount of the immunogenic composition as claimed in claim 1 to a patient.

4. The method as claimed in claim 3, wherein said administering comprises administration by injection.

5. The method as claimed in claim 3, wherein said administering results in an eight-fold rise in antibody titer.

6. A method for the manufacture of the immunogenic composition as claimed in claim 1, comprising:

providing the antigenic components;

conjugating each antigen in each antigenic component to the carrier molecule; and preparing each conjugated antigen at a dose of about 5 μg/dose to about 30 μg/dose.

7. The method as claimed in claim 6, wherein said conjugating is performed by:

carbodiimide mediated modification of the antigen with adipic acid dihydrazide (ADH) introducing reactive hydrazide groups that are then used to link to the carrier molecule via a second carbodiimide step;

derivatization of the antigen with an amine reactive reagent succinimidyl 4-maleimidylbutyrate (GMBS) that introduces a maleimide moiety that is then linked to a reactive sulfhydryl of the derivatized molecule via formation of a thio ether bond; or 1-cyano-4-(dimethylamino)-pyridinium tetrafluoroborate (CDAP) chemistry.

8. The immunogenic composition as claimed in claim 1, wherein the one or more carrier molecules comprise two or more carrier molecules.

9. The immunogenic composition as claimed in claim 8, wherein the two or more carrier molecules comprise more than two carrier molecules.

10. The immunogenic composition as claimed in claim 1, wherein the one or more carrier molecules comprise one or more of tetanus toxin, tetanus toxin heavy chain proteins, diphtheria toxoid, tetanus toxoid, *Pseudomonas* exoprotein A, *Pseudomonas aeruginosa* toxoid, *Bordetella pertusis* toxoid, *Clostridium perfringens* toxoid, *Escherichia coli* heat-labile toxin B subunit, *Neisseria meningitidis* outer membrane complex, recombinant exoprotein A (rEPA), *Hemophilus influenzae* protein D, Flagellin FliC, Horseshoe crab Haemocyanin, and fragments, derivatives, and modifications thereof.

11. The immunogenic composition as claimed in claim 1, wherein the one or more carrier molecules comprise one or more of tetanus toxin, tetanus toxin heavy chain proteins, diphtheria toxoid, *Pseudomonas* exoprotein A, *Pseudomonas aeruginosa* toxoid, *Bordetella pertusis* toxoid,

*Clostridium perfringens* toxoid, *Escherichia coli* heat-labile toxin B subunit, *Neisseria meningitidis* outer membrane complex, recombinant exoprotein A (rEPA), *Hemophilus influenzae* protein D, Flagellin FliC, Horseshoe crab Haemocyanin, and fragments, derivatives, and modifications thereof.

12. The immunogenic composition as claimed in claim 1, wherein the one or more carrier molecules comprise one or more of tetanus toxin, tetanus toxin heavy chain proteins, diphtheria toxoid, tetanus toxoid, *Pseudomonas* exoprotein A, *Pseudomonas aeruginosa* toxoid, *Bordetella pertusis* toxoid, *Clostridium perfringens* toxoid, *Escherichia coli* heat-labile toxin B subunit, *Neisseria meningitidis* outer membrane complex, recombinant exoprotein A (rEPA), *Hemophilus influenzae* protein D, Horseshoe crab Haemocyanin, and fragments, derivatives, and modifications thereof.

13. The immunogenic composition as claimed in claim 1, wherein the one or more carrier molecules comprise one or more of tetanus toxin, tetanus toxin heavy chain proteins, diphtheria toxoid, *Pseudomonas* exoprotein A, *Pseudomonas aeruginosa* toxoid, *Bordetella pertusis* toxoid, *Clostridium perfringens* toxoid, *Escherichia coli* heat-labile toxin B subunit, *Neisseria meningitidis* outer membrane complex, recombinant exoprotein A (rEPA), *Hemophilus influenzae* protein D, Horseshoe crab Haemocyanin, and fragments, derivatives, and modifications thereof.

14. The immunogenic composition as claimed in claim 1, wherein the bivalent or trivalent antigenic component is (i).

15. The immunogenic composition as claimed in claim 1, wherein the bivalent or trivalent antigenic component is (ii).

16. The immunogenic composition as claimed in claim 1, wherein the bivalent or trivalent antigenic component is (iii).

17. The immunogenic composition as claimed in claim 1, wherein said at least one pharmaceutically acceptable substance comprises a stabilizer, a buffer, a preservative, an amino acid, a salt, a bulking agent, an antioxidant, a dispersant, one or more adjuvants, or combinations thereof.

* * * * *